United States Patent
Jacobsen et al.

(10) Patent No.: US 9,060,704 B2
(45) Date of Patent: Jun. 23, 2015

(54) METHOD AND DEVICE FOR WAVELENGTH SHIFTED IMAGING

(75) Inventors: Stephen C. Jacobsen, Salt Lake City, UT (US); David P. Marceau, Salt Lake City, UT (US)

(73) Assignee: Sarcos LC, Salt Lake City, UT (US)

( * ) Notice: Subject to any disclaimer, the term of this patent is extended or adjusted under 35 U.S.C. 154(b) by 826 days.

(21) Appl. No.: 12/611,776

(22) Filed: Nov. 3, 2009

(65) Prior Publication Data

US 2010/0171821 A1  Jul. 8, 2010

Related U.S. Application Data

(60) Provisional application No. 61/111,162, filed on Nov. 4, 2008.

(51) Int. Cl.
| | | |
|---|---|---|
| H04N 1/04 | (2006.01) |
| A61B 1/05 | (2006.01) |
| A61B 1/00 | (2006.01) |
| A61B 1/06 | (2006.01) |
| A61M 25/01 | (2006.01) |

(52) U.S. Cl.
CPC .............. *A61B 1/05* (2013.01); *A61B 1/00096* (2013.01); *A61B 1/0638* (2013.01); *A61M 25/0138* (2013.01)

(58) Field of Classification Search
None
See application file for complete search history.

(56) References Cited

U.S. PATENT DOCUMENTS

| | | |
|---|---|---|
| 3,787,121 A | 1/1974 | Lowy et al. |
| 3,817,635 A | 6/1974 | Kawahar |
| 3,856,000 A | 12/1974 | Chikama |
| 3,886,933 A | 6/1975 | Mori et al. |
| 3,918,438 A | 11/1975 | Hayamizu et al. |
| 3,971,065 A | 7/1976 | Bayer |
| 4,277,168 A | 7/1981 | Oku |
| 4,283,115 A | 8/1981 | Fraissl |

(Continued)

FOREIGN PATENT DOCUMENTS

| | | |
|---|---|---|
| CN | 1481753 | 3/2004 |
| DE | 197 42 973 | 4/1998 |

(Continued)

OTHER PUBLICATIONS

PCT Application PCT/US2010/051200; filed Oct. 1, 2010; Stephen C. Jacobsen; ISR mailed Jun. 3, 2011.

(Continued)

*Primary Examiner* — Philip Chea
*Assistant Examiner* — Van Kim T Nguyen
(74) *Attorney, Agent, or Firm* — Thorpe North & Westerner, LLP

(57) ABSTRACT

A micro-camera catheter device is disclosed comprising at least one light source disposed on a distal end of a catheter. The light source is capable of propagating a predetermined wavelength of light with a wavelength between approximately 1000 nanometers and approximately 2000 nanometers onto a target. The device further comprises a lens system disposed on the distal end of the catheter, said lens system configured to receive light reflected from the target. The device further comprises a non-linear optical media disposed behind the lens system configured to modify the light reflected from the target. The device also comprises a silicon-based solid state imaging device disposed behind the non-linear optical media configured to receive light from the non-linear optical media.

21 Claims, 3 Drawing Sheets

(56) References Cited

U.S. PATENT DOCUMENTS

| | | |
|---|---|---|
| 4,349,456 A | 9/1982 | Sowman |
| 4,360,275 A | 11/1982 | Louderback |
| 4,403,985 A | 9/1983 | Boretos |
| 4,475,902 A | 10/1984 | Schubert |
| 4,487,206 A | 12/1984 | Aagard |
| 4,491,865 A | 1/1985 | Danna et al. |
| 4,515,444 A | 5/1985 | Prescott et al. |
| 4,573,450 A | 3/1986 | Arakawa |
| 4,585,349 A | 4/1986 | Gross et al. |
| 4,588,294 A | 5/1986 | Siegmund |
| 4,589,404 A | 5/1986 | Barath et al. |
| 4,593,313 A | 6/1986 | Nagasaki et al. |
| 4,594,613 A | 6/1986 | Shinbori et al. |
| 4,600,831 A | 7/1986 | Hutley |
| 4,604,992 A | 8/1986 | Sato |
| 4,620,534 A | 11/1986 | Zartman |
| 4,621,284 A | 11/1986 | Nishioka et al. |
| 4,622,954 A | 11/1986 | Arakawa et al. |
| 4,626,079 A | 12/1986 | Nakamura et al. |
| 4,641,927 A | 2/1987 | Prescott et al. |
| 4,646,724 A | 3/1987 | Sato et al. |
| 4,672,218 A | 6/1987 | Chrisman et al. |
| 4,706,118 A | 11/1987 | Kato et al. |
| 4,707,134 A | 11/1987 | McLachlan et al. |
| 4,723,843 A | 2/1988 | Zobel |
| 4,725,721 A | 2/1988 | Nakamura |
| 4,745,470 A | 5/1988 | Yabe et al. |
| 4,745,471 A | 5/1988 | Takamura et al. |
| 4,783,591 A | 11/1988 | Sullivan |
| 4,785,815 A | 11/1988 | Cohen |
| 4,790,624 A | 12/1988 | Van Hoye et al. |
| 4,791,479 A | 12/1988 | Ogiu et al. |
| 4,802,487 A | 2/1989 | Martin et al. |
| 4,803,562 A | 2/1989 | Eino |
| 4,832,003 A | 5/1989 | Yabe |
| 4,843,416 A | 6/1989 | Brower |
| 4,846,785 A | 7/1989 | Cassou et al. |
| 4,859,040 A | 8/1989 | Kitagishi et al. |
| 4,867,137 A | 9/1989 | Takahashi |
| 4,867,138 A | 9/1989 | Kubota et al. |
| 4,867,174 A | 9/1989 | Skribiski |
| 4,880,298 A | 11/1989 | Takada |
| 4,895,138 A | 1/1990 | Yabe |
| 4,916,534 A | 4/1990 | Takhashi et al. |
| 4,926,257 A | 5/1990 | Miyazaki |
| 4,930,880 A | 6/1990 | Miyauchi |
| 4,932,394 A | 6/1990 | Nanaumi |
| 4,934,340 A | 6/1990 | Ebling et al. |
| 4,941,457 A | 7/1990 | Hasegawa |
| 4,998,807 A | 3/1991 | Uzawa et al. |
| 5,006,928 A | 4/1991 | Kawajiri et al. |
| 5,009,483 A | 4/1991 | Rockwell, III |
| 5,021,888 A | 6/1991 | Kondou et al. |
| 5,022,972 A | 6/1991 | David et al. |
| 5,032,913 A | 7/1991 | Hattori et al. |
| 5,040,069 A | 8/1991 | Matsumoto et al. |
| 5,061,036 A | 10/1991 | Gordon |
| 5,093,719 A | 3/1992 | Prescott |
| 5,105,269 A | 4/1992 | Nakamura et al. |
| 5,106,387 A | 4/1992 | Kittrell et al. |
| 5,109,859 A | 5/1992 | Jenkins |
| 5,111,804 A | 5/1992 | Funakoshi |
| 5,113,254 A | 5/1992 | Kanno et al. |
| 5,121,213 A | 6/1992 | Nishioka |
| 5,126,639 A | 6/1992 | Srivastava |
| 5,130,804 A | 7/1992 | Tamura et al. |
| 5,165,063 A | 11/1992 | Strater et al. |
| 5,166,656 A | 11/1992 | Badehi et al. |
| 5,182,672 A | 1/1993 | Mukai et al. |
| 5,188,093 A | 2/1993 | Lafferty et al. |
| 5,190,523 A | 3/1993 | Lindmayer |
| 5,191,203 A | 3/1993 | McKinley |
| 5,198,894 A | 3/1993 | Hicks |
| 5,209,219 A | 5/1993 | Hollobaugh |
| 5,220,198 A | 6/1993 | Tsuji |
| 5,222,477 A | 6/1993 | Lia |
| 5,228,430 A | 7/1993 | Sakamoto |
| 5,258,834 A | 11/1993 | Tsuji et al. |
| 5,289,434 A | 2/1994 | Berni |
| 5,290,555 A | 3/1994 | Guthauser et al. |
| 5,291,010 A | 3/1994 | Tsuji |
| 5,298,741 A | 3/1994 | Walt et al. |
| 5,304,173 A | 4/1994 | Kittrell et al. |
| 5,305,098 A | 4/1994 | Matsunaka et al. |
| 5,318,024 A | 6/1994 | Kittrell et al. |
| 5,361,166 A | 11/1994 | Atkinson et al. |
| 5,365,268 A | 11/1994 | Minami |
| 5,376,960 A | 12/1994 | Wurster |
| 5,377,047 A | 12/1994 | Broome et al. |
| 5,381,784 A | 1/1995 | Adair |
| 5,396,366 A | 3/1995 | Brown et al. |
| 5,398,685 A | 3/1995 | Wilk et al. |
| 5,402,769 A | 4/1995 | Tsuji |
| 5,408,999 A | 4/1995 | Singh et al. |
| 5,430,475 A | 7/1995 | Goto et al. |
| 5,434,615 A | 7/1995 | Matumoto |
| 5,436,655 A | 7/1995 | Hiyama et al. |
| 5,438,975 A | 8/1995 | Miyagi et al. |
| 5,440,669 A | 8/1995 | Rakuljie et al. |
| 5,450,243 A | 9/1995 | Nishioka |
| 5,455,455 A | 10/1995 | Badehi |
| 5,458,612 A | 10/1995 | Chin |
| 5,459,570 A | 10/1995 | Swanson et al. |
| 5,469,841 A | 11/1995 | Kobayashi et al. |
| 5,494,483 A | 2/1996 | Adair |
| 5,512,940 A | 4/1996 | Takasugi et al. |
| 5,517,997 A | 5/1996 | Fontenot |
| 5,531,664 A | 7/1996 | Adachi et al. |
| 5,547,455 A | 8/1996 | McKenna et al. |
| 5,547,906 A | 8/1996 | Badehi |
| 5,594,497 A | 1/1997 | Ahern |
| 5,603,687 A | 2/1997 | Hori et al. |
| 5,607,435 A | 3/1997 | Sachdeva et al. |
| 5,621,574 A | 4/1997 | Foo |
| 5,630,788 A | 5/1997 | Forkner et al. |
| 5,647,368 A | 7/1997 | Zeng et al. |
| 5,662,621 A | 9/1997 | Lafontaine |
| 5,673,083 A | 9/1997 | Izumi et al. |
| 5,685,311 A | 11/1997 | Hara |
| 5,693,043 A | 12/1997 | Kittrell et al. |
| 5,704,892 A | 1/1998 | Adair |
| 5,716,323 A | 2/1998 | Lee |
| 5,716,759 A | 2/1998 | Badehi |
| 5,722,403 A | 3/1998 | McGee et al. |
| 5,732,150 A | 3/1998 | Zhou et al. |
| 5,740,808 A | 4/1998 | Panescu et al. |
| 5,749,827 A | 5/1998 | Minami |
| 5,751,340 A | 5/1998 | Strobl et al. |
| 5,752,518 A | 5/1998 | McGee et al. |
| 5,769,792 A | 6/1998 | Palcic et al. |
| 5,772,597 A | 6/1998 | Goldberger et al. |
| 5,776,049 A | 7/1998 | Takahashi |
| 5,783,829 A | 7/1998 | Sealock et al. |
| 5,784,098 A | 7/1998 | Shoji et al. |
| 5,792,984 A | 8/1998 | Bloom |
| 5,800,341 A | 9/1998 | McKenna et al. |
| 5,807,261 A | 9/1998 | Benaron et al. |
| 5,808,665 A | 9/1998 | Green |
| 5,818,644 A | 10/1998 | Noda |
| 5,827,172 A | 10/1998 | Takahashi et al. |
| 5,827,531 A | 10/1998 | Morrison et al. |
| 5,840,017 A | 11/1998 | Furusawa et al. |
| 5,846,185 A | 12/1998 | Carollo |
| 5,848,969 A | 12/1998 | Panescu et al. |
| 5,865,729 A | 2/1999 | Meehan et al. |
| 5,870,229 A | 2/1999 | Tsuchuda |
| 5,873,816 A | 2/1999 | Kagawa et al. |
| 5,879,285 A | 3/1999 | Ishii |
| 5,904,651 A | 5/1999 | Swanson et al. |
| 5,908,445 A | 6/1999 | Whayne et al. |
| 5,913,817 A | 6/1999 | Lee |
| 5,916,155 A | 6/1999 | Levinson et al. |
| 5,929,900 A | 7/1999 | Yamanaka et al. |
| 5,940,126 A | 8/1999 | Kimura |

(56) References Cited

U.S. PATENT DOCUMENTS

| | | |
|---|---|---|
| 5,947,894 A | 9/1999 | Chapman et al. |
| 5,951,462 A | 9/1999 | Yamanaka |
| 5,957,849 A | 9/1999 | Munro |
| 5,971,915 A | 10/1999 | Yamamoto et al. |
| 5,973,779 A | 10/1999 | Ansari et al. |
| 5,980,663 A | 11/1999 | Badehi |
| 5,989,185 A | 11/1999 | Miyazaki |
| 5,998,878 A | 12/1999 | Johnson |
| 5,999,327 A | 12/1999 | Nagaoka |
| 6,008,123 A | 12/1999 | Kook et al. |
| 6,014,919 A | 1/2000 | Jacobsen et al. |
| 6,022,758 A | 2/2000 | Badehi |
| 6,040,235 A | 3/2000 | Badehi |
| 6,059,760 A | 5/2000 | Sandmore et al. |
| 6,095,970 A | 8/2000 | Hidaka et al. |
| 6,117,707 A | 9/2000 | Badehi |
| 6,118,476 A | 9/2000 | Morito et al. |
| 6,133,637 A | 10/2000 | Hikita et al. |
| 6,134,003 A | 10/2000 | Terney et al. |
| 6,139,489 A | 10/2000 | Wampler et al. |
| 6,139,819 A | 10/2000 | Unger et al. |
| 6,142,930 A | 11/2000 | Ito et al. |
| 6,161,035 A | 12/2000 | Furusawa |
| 6,184,923 B1 | 2/2001 | Miyazaki |
| 6,193,908 B1 | 2/2001 | Hampden-Smith et al. |
| 6,211,955 B1 | 4/2001 | Basiji et al. |
| 6,224,969 B1 | 5/2001 | Steenbergen et al. |
| 6,261,226 B1 | 7/2001 | McKenna et al. |
| 6,262,855 B1 | 7/2001 | Greisz |
| 6,271,206 B1 | 8/2001 | Pillai et al. |
| 6,280,960 B1 | 8/2001 | Carr |
| 6,288,172 B1 | 9/2001 | Goetz et al. |
| 6,319,745 B1 | 11/2001 | Bertin et al. |
| 6,322,498 B1 | 11/2001 | Gravenstein et al. |
| 6,327,096 B1 | 12/2001 | Tsuchida |
| 6,352,503 B1 | 3/2002 | Matsue |
| 6,361,491 B1 | 3/2002 | Hasegawa et al. |
| 6,366,726 B1 | 4/2002 | Wach et al. |
| 6,375,635 B1 | 4/2002 | Moutafis et al. |
| 6,384,397 B1 | 5/2002 | Takiar et al. |
| 6,384,884 B1 | 5/2002 | Nakamura et al. |
| 6,396,116 B1 | 5/2002 | Kelly et al. |
| 6,407,768 B1 | 6/2002 | Ishikaw |
| 6,445,939 B1 | 9/2002 | Swanson et al. |
| 6,456,423 B1 | 9/2002 | Nayfeh et al. |
| 6,471,636 B1 | 10/2002 | Sano et al. |
| 6,485,413 B1 | 11/2002 | Boppart et al. |
| 6,522,913 B2 | 2/2003 | Swanson et al. |
| 6,525,866 B1 | 2/2003 | Lin et al. |
| 6,533,722 B2 | 3/2003 | Nakashima |
| 6,537,205 B1 | 3/2003 | Smith |
| 6,551,302 B1 | 4/2003 | Rosinko et al. |
| 6,552,796 B2 | 4/2003 | Magnin et al. |
| 6,561,972 B2 | 5/2003 | Ooshima et al. |
| 6,570,659 B2 | 5/2003 | Schmitt |
| 6,573,950 B1 | 6/2003 | Hirata et al. |
| 6,585,717 B1 | 7/2003 | Wittenberg et al. |
| 6,595,913 B2 | 7/2003 | Takahashi |
| 6,618,614 B1 | 9/2003 | Chance et al. |
| 6,622,373 B1 | 9/2003 | Tu et al. |
| 6,643,071 B2 | 11/2003 | Schnitzer |
| 6,658,279 B2 | 12/2003 | Swanson et al. |
| 6,659,941 B2 | 12/2003 | Weber et al. |
| 6,695,787 B2 | 2/2004 | Hogenkijk et al. |
| 6,710,919 B1 | 3/2004 | Clausen |
| 6,719,686 B2 | 4/2004 | Coakley et al. |
| 6,727,313 B2 | 4/2004 | Zhou et al. |
| 6,756,437 B1 | 6/2004 | Xue et al. |
| 6,761,684 B1 | 7/2004 | Speier |
| 6,785,048 B2 | 8/2004 | Yamaguchi et al. |
| 6,826,422 B1 | 11/2004 | Modell et al. |
| 6,827,683 B2 | 12/2004 | Otawara |
| 6,833,916 B2 | 12/2004 | Osipchuk et al. |
| 6,834,158 B1 | 12/2004 | Templeton |
| 6,842,288 B1 | 1/2005 | Liu et al. |
| 6,850,659 B2 | 2/2005 | Han |
| 6,879,851 B2 | 4/2005 | McNamara et al. |
| 6,881,448 B1 | 4/2005 | Hattori |
| 6,891,984 B2 | 5/2005 | Petersen et al. |
| 6,893,432 B2 | 5/2005 | Intintoli et al. |
| 6,894,729 B2 | 5/2005 | Hirata et al. |
| 6,898,458 B2 | 5/2005 | Zeng et al. |
| 6,900,913 B2 | 5/2005 | Chen |
| 6,930,705 B2 | 8/2005 | Tanaka |
| 6,937,268 B2 | 8/2005 | Ogawa |
| 6,939,348 B2 | 9/2005 | Malecki et al. |
| 6,941,041 B2 | 9/2005 | Yamaguchi et al. |
| 6,944,204 B2 | 9/2005 | Zhou et al. |
| 6,953,432 B2 | 10/2005 | Schiefer |
| 6,956,624 B2 | 10/2005 | Hirata et al. |
| 6,960,165 B2 | 11/2005 | Ueno et al. |
| 6,982,740 B2 | 1/2006 | Adair et al. |
| 6,990,271 B2 | 1/2006 | Gafsi et al. |
| 7,030,904 B2 | 4/2006 | Adair et al. |
| 7,033,317 B2 | 4/2006 | Pruitt |
| 7,058,294 B2 | 6/2006 | Nakahara |
| 7,075,576 B2 | 7/2006 | Creasey et al. |
| 7,081,927 B2 | 7/2006 | Hirata et al. |
| 7,091,500 B2 | 8/2006 | Schnitzer |
| 7,098,871 B1 | 8/2006 | Tegreene et al. |
| 7,102,817 B1 | 9/2006 | Wu |
| 7,108,657 B2 | 9/2006 | Irion et al. |
| 7,153,299 B1 | 12/2006 | Tu et al. |
| 7,165,552 B2 | 1/2007 | Deem et al. |
| 7,166,537 B2 | 1/2007 | Jacobsen |
| 7,167,317 B2 | 1/2007 | Jung et al. |
| 7,186,251 B2 | 3/2007 | Malecki et al. |
| 7,218,822 B2 | 5/2007 | Treado et al. |
| 7,221,388 B2 | 5/2007 | Sudo et al. |
| 7,234,816 B2 | 6/2007 | Bruzzone et al. |
| 7,247,847 B2 | 7/2007 | Webb et al. |
| 7,304,310 B1 | 12/2007 | Shortt et al. |
| 7,393,321 B2 | 7/2008 | Doguchi et al. |
| 7,420,675 B2 | 9/2008 | Giakos |
| 7,433,552 B2 | 10/2008 | Kiesel et al. |
| 7,511,891 B2 | 3/2009 | Messerschmidt |
| 7,554,597 B2 | 6/2009 | Scherling |
| 7,591,780 B2 | 9/2009 | Jacobsen |
| 7,629,659 B2 | 12/2009 | Jacobsen |
| 7,787,939 B2 | 8/2010 | Jacobsen et al. |
| 7,823,215 B2 | 10/2010 | Giakos |
| 7,835,074 B2 | 11/2010 | Jacobsen et al. |
| 7,842,046 B1 | 11/2010 | Nakao |
| 7,901,870 B1 | 3/2011 | Wach |
| 2001/0007051 A1 | 7/2001 | Nakashima |
| 2001/0007511 A1 | 7/2001 | Minami et al. |
| 2001/0012053 A1 | 8/2001 | Nakamura |
| 2001/0024848 A1 | 9/2001 | Nakamura |
| 2001/0049509 A1 | 12/2001 | Sekine et al. |
| 2002/0007110 A1 | 1/2002 | Irion |
| 2002/0034537 A1 | 3/2002 | Schulze et al. |
| 2002/0039594 A1 | 4/2002 | Unger |
| 2002/0080248 A1 | 6/2002 | Adair et al. |
| 2002/0109774 A1 | 8/2002 | Meron et al. |
| 2002/0111534 A1 | 8/2002 | Suzuki et al. |
| 2002/0166946 A1 | 11/2002 | Iizuka et al. |
| 2002/0168776 A1 | 11/2002 | Cizdziel et al. |
| 2002/0188204 A1 | 12/2002 | McNamara |
| 2002/0193660 A1 | 12/2002 | Weber |
| 2003/0071342 A1 | 4/2003 | Honda et al. |
| 2003/0092995 A1 | 5/2003 | Thompson |
| 2003/0114732 A1 | 6/2003 | Webler et al. |
| 2003/0197812 A1 | 10/2003 | Hirata et al. |
| 2003/0199761 A1 | 10/2003 | Yock |
| 2003/0202127 A1 | 10/2003 | Hirata et al. |
| 2003/0208211 A1 | 11/2003 | Kortenbach |
| 2003/0220574 A1 | 11/2003 | Markus |
| 2003/0222325 A1 | 12/2003 | Jacobsen |
| 2004/0006274 A1 | 1/2004 | Giller et al. |
| 2004/0015049 A1 | 1/2004 | Zaar |
| 2004/0017961 A1 | 1/2004 | Petersen et al. |
| 2004/0059204 A1 | 3/2004 | Marshall |
| 2004/0097804 A1 | 5/2004 | Sobe |
| 2004/0111031 A1 | 6/2004 | Alfano et al. |

(56) References Cited

U.S. PATENT DOCUMENTS

| | | | |
|---|---|---|---|
| 2004/0115955 A1 | 6/2004 | Motoyama et al. | |
| 2004/0165858 A1* | 8/2004 | Curatolo | 385/147 |
| 2004/0181148 A1 | 9/2004 | Uchiyama et al. | |
| 2004/0222031 A1 | 11/2004 | Szalony et al. | |
| 2004/0225222 A1 | 11/2004 | Zeng et al. | |
| 2004/0257566 A1 | 12/2004 | Chism | |
| 2004/0260148 A1* | 12/2004 | Schnitzer | 600/108 |
| 2005/0054902 A1 | 3/2005 | Konno | |
| 2005/0065504 A1 | 3/2005 | Melsky et al. | |
| 2005/0084229 A1 | 4/2005 | Babbitt et al. | |
| 2005/0088576 A1 | 4/2005 | Hirata et al. | |
| 2005/0099824 A1 | 5/2005 | Dowling et al. | |
| 2005/0110892 A1 | 5/2005 | Yun | |
| 2005/0124875 A1 | 6/2005 | Kawano et al. | |
| 2005/0152421 A1 | 7/2005 | Fujitani | |
| 2005/0154277 A1 | 7/2005 | Tang et al. | |
| 2005/0158899 A1* | 7/2005 | Jacobsen et al. | 438/29 |
| 2005/0171521 A1 | 8/2005 | Brucker et al. | |
| 2005/0174649 A1 | 8/2005 | Okada et al. | |
| 2005/0187568 A1 | 8/2005 | Klenk et al. | |
| 2005/0197534 A1 | 9/2005 | Barbato et al. | |
| 2005/0226636 A1 | 10/2005 | Hiramatsu et al. | |
| 2005/0231718 A1 | 10/2005 | Goodall et al. | |
| 2005/0234345 A1 | 10/2005 | Yang | |
| 2005/0264813 A1 | 12/2005 | Giakos | |
| 2005/0267340 A1 | 12/2005 | Ishihara et al. | |
| 2005/0288555 A1 | 12/2005 | Binmoeller | |
| 2006/0009682 A1 | 1/2006 | Nagasawa et al. | |
| 2006/0013593 A1* | 1/2006 | Yokoo et al. | 398/152 |
| 2006/0017928 A1* | 1/2006 | Crowther | 356/419 |
| 2006/0051036 A1 | 3/2006 | Treado | |
| 2006/0069312 A1 | 3/2006 | O'Connor | |
| 2006/0079835 A1 | 4/2006 | Frassica | |
| 2006/0106283 A1 | 5/2006 | Wallace et al. | |
| 2006/0135921 A1 | 6/2006 | Wiercinski et al. | |
| 2006/0142700 A1 | 6/2006 | Sobelman et al. | |
| 2006/0146172 A1* | 7/2006 | Jacobsen et al. | 348/340 |
| 2006/0161048 A1 | 7/2006 | Squicciarini | |
| 2006/0181774 A1 | 8/2006 | Ojima et al. | |
| 2006/0252994 A1 | 11/2006 | Ratnakar | |
| 2006/0253088 A1 | 11/2006 | Chow et al. | |
| 2007/0010709 A1 | 1/2007 | Reinschke | |
| 2007/0032796 A1 | 2/2007 | Chin-Chen et al. | |
| 2007/0073321 A1 | 3/2007 | Mikkaichi et al. | |
| 2007/0083232 A1 | 4/2007 | Lee | |
| 2007/0088276 A1 | 4/2007 | Stubbs et al. | |
| 2007/0135803 A1 | 6/2007 | Belson | |
| 2007/0146887 A1 | 6/2007 | Ikeda et al. | |
| 2007/0208252 A1 | 9/2007 | Makower | |
| 2007/0228300 A1* | 10/2007 | Smith | 250/504 R |
| 2007/0233187 A1 | 10/2007 | Lobello | |
| 2007/0239066 A1 | 10/2007 | Laham et al. | |
| 2007/0255392 A1 | 11/2007 | Johnson | |
| 2007/0293727 A1 | 12/2007 | Goldfarb et al. | |
| 2008/0045794 A1 | 2/2008 | Belson | |
| 2008/0058601 A1 | 3/2008 | Fujimori | |
| 2008/0071141 A1 | 3/2008 | Gattani et al. | |
| 2008/0094326 A1 | 4/2008 | Yamaki et al. | |
| 2008/0114309 A1 | 5/2008 | Zuckerman | |
| 2008/0160257 A1 | 7/2008 | Takada et al. | |
| 2008/0177141 A1 | 7/2008 | Wu et al. | |
| 2008/0183080 A1 | 7/2008 | Abraham | |
| 2008/0188767 A1 | 8/2008 | Oaki et al. | |
| 2008/0227893 A1 | 9/2008 | Tamori et al. | |
| 2008/0267562 A1 | 10/2008 | Wang et al. | |
| 2009/0027765 A1* | 1/2009 | Kamijima | 359/328 |
| 2009/0036764 A1 | 2/2009 | Rivas et al. | |
| 2009/0054791 A1 | 2/2009 | Flusberg | |
| 2009/0082626 A1 | 3/2009 | Ichimura et al. | |
| 2009/0119808 A1 | 5/2009 | Giakos | |
| 2009/0137928 A1 | 5/2009 | Quick et al. | |
| 2009/0143645 A1 | 6/2009 | Matthes | |
| 2009/0155371 A1 | 6/2009 | Sojka et al. | |
| 2009/0156899 A1 | 6/2009 | Konishi | |
| 2009/0180197 A1 | 7/2009 | Jacobsen et al. | |
| 2009/0213894 A1* | 8/2009 | Grapov et al. | 372/107 |
| 2009/0234325 A1 | 9/2009 | Rozenberg et al. | |
| 2009/0267270 A1 | 10/2009 | Murakami et al. | |
| 2009/0287048 A1 | 11/2009 | Jacobson et al. | |
| 2010/0085567 A1* | 4/2010 | Dottery et al. | 356/301 |
| 2010/0106134 A1 | 4/2010 | Jolly et al. | |
| 2010/0134872 A1 | 6/2010 | Johnson et al. | |
| 2010/0171821 A1* | 7/2010 | Jacobsen et al. | 348/68 |
| 2010/0248178 A1 | 9/2010 | Nahlieli | |
| 2011/0204265 A1* | 8/2011 | Smith et al. | 250/503.1 |

FOREIGN PATENT DOCUMENTS

| | | |
|---|---|---|
| DE | 19859434 | 7/2000 |
| EP | 0482997 | 4/1992 |
| EP | 0550 995 | 7/1993 |
| EP | 0639043 | 2/1995 |
| EP | 0681809 | 11/1995 |
| EP | 1104182 | 5/2001 |
| EP | 1195130 | 4/2002 |
| EP | 1477104 | 11/2004 |
| EP | 1488737 | 12/2004 |
| EP | 1626436 | 2/2006 |
| EP | 1647569 | 4/2006 |
| EP | 1880656 | 1/2008 |
| JP | 58-046924 | 3/1983 |
| JP | 63-155115 | 6/1988 |
| JP | H05-039501 | 2/1993 |
| JP | 5-049602 | 3/1993 |
| JP | H07-148105 | 6/1995 |
| JP | H07-222712 | 8/1995 |
| JP | 08-076028 | 3/1996 |
| JP | 08084700 | 4/1996 |
| JP | H09-021963 | 1/1997 |
| JP | 11 137512 | 5/1999 |
| JP | 2001/314365 | 11/2001 |
| JP | 2004-086553 | 3/2004 |
| JP | 2004/329700 | 11/2004 |
| JP | 2005334462 | 8/2005 |
| JP | 2006/162418 | 6/2006 |
| JP | 2006/320369 | 11/2006 |
| JP | 2007-167387 | 7/2007 |
| JP | 2007/312290 | 11/2007 |
| JP | 2009/067946 | 4/2009 |
| KR | 10-20080027935 | 3/2008 |
| WO | WO98/38907 | 9/1998 |
| WO | WO99/40624 | 8/1999 |
| WO | WO00/54033 | 9/2000 |
| WO | WO 03/081831 | 10/2003 |
| WO | WO2006/060777 | 6/2006 |

OTHER PUBLICATIONS

PCT Application PCT/US2010/051198; filed Oct. 1, 2010; Stephen C. Jacobsen; ISR mailed Jun. 3, 2011.

PCT Application PCT/US2010/051192; filed Oct. 1, 2010; Stephen C. Jacobsen; ISR mailed May 30, 2011.

Gaoping et al.; Research on the Measurement of Grin Lens Focused Spot Diameter and Resolution; Applied Optics; 1995; vol. 16, No. 6.

PCT Application PCT/US2010/051188; filed Oct. 1, 2010; Stephen C. Jacobsen; International Search Report mailed Jul. 13, 2011.

Xie et al; GRIN Lens Rod Based Probe for Endoscopic Spectral Domain Optical Coherence Tomography with Fast Dynamic Focus Tracking; Optics Express; Apr. 17, 2006; 9 pages; vol. 14, No. 8.

Xuting Technologies Co., Ltd.; http://www.xutingby.com/en/products/glinfo.htm; as accessed May 1, 2008; 5 pages.

Frequency; Wikipedia, The Free Encyclopedia; http://en.wikipedia.org/wiki/Frequency; as accessed May 9, 2008; 4 pages.

Introduction to Gradient Index Optics; http://grintech.de/e_main_grin.htm; as accessed May 1, 2008; 7 pages.

Gradient Index (GRIN) Lenses; Grin Tech; 2 pages; The Applicant believes the year of publication of this article is prior to the effective US filing date of this patent application.

Shape Memory Polymers—Biodegradable Sutures; http://www.azom.com/details.asp?ArticleID=1542; as accessed Nov. 6, 2007; 4 pages.

(56) References Cited

OTHER PUBLICATIONS

Surgical Needles for Use With Sutures; Wikipedia, The Free Encyclopedia; as accessed Nov. 6, 2007; 6 pages.

Harder et al; Against the Migraine; Science News Online; http://www.sciencenews.org/articles/20050219/bob8.asp; Feb. 19, 2005; 11 pages.

U.S. Appl. No. 12/152,730, filed May 16, 2008; Stephen C. Jacobson; office action issued Sep. 16, 2011.

Johansson et al., "Generation of turquoise light by sum frequency mixing of a diode-pumped solid-state laser and a laser diode in periodically poled KTP," Optics Express, Oct. 4, 2004, pp. 4935-4940, vol. 12, No. 12.

http://news.thomasnet.com/fullstory/23462, "Near-IR camera utilizes CCD array with phosphor coating," Jun. 11, 2003, 5 pages.

Boppart, S.A. et al., "Forward-imaging instruments for optical coherence tomography." Optics Letters, Nov. 1, 1997, vol. 22, No. 21, pp. 1618-1620.

Boppart, S.A. et al., "Optical imaging technology in minimally invasive surgery," Surg. Endosc., 1999, vol. 13, pp. 718-722.

Fujimoto, JG et al., "High resolution in vivo intra-arterial imaging with optical coherence tomography," Heart, 1999, vol. 82, pp. 128-133.

Hirofumi Tsuchida et al., "Design of imaging lens systems that use low dispersive radial gradient-index rod," Jpn, J. Appl. Phys. vol. 37 No. 6B, Jun. 30, 1998, pp. 3633-3637.

J. Knittel et al., "Endoscope-compatible confocal microscope using a gradient index-lens system" Optics Communications, vol. 188, Issue 5-6, Feb. 2001, pp. 267-273.

Jacobsen, Stephen C., U.S. Appl. No. 10/391,489, filed Mar. 17, 2003.

Jacobsen, Stephen C., U.S. Appl. No. 10/391,490, filed Mar. 17, 2003.

Jacobsen, Stephen C., U.S. Appl. No. 10/391,513, filed Mar. 17, 2003.

Jacobsen, Stephen C., U.S. Appl. No. 11/292,902, filed Dec. 1, 2005.

Jacobsen, Stephen C., U.S. Appl. No. 11/810,702, filed Jun. 5, 2007.

Jacobsen, Stephen C., U.S. Appl. No. 12/008,486, filed Jan. 11, 2008.

Jacobsen, Stephen C., U.S. Appl. No. 12/079,741, filed Mar. 27, 2008.

Jacobsen, Stephen C., U.S. Appl. No. 12/152,730, filed May 16, 2008.

Jacobsen, Stephen C., U.S. Appl. No. 12/512,188, filed Jul. 30, 2009.

Literature from GRIN Tech, "In vivo medical confocal imaging and optical coherence tomography," www.grintech.de, Revision Jun. 2001, pp. 1-3.

Microcam, MINAST Project 5.04, Nov. 11, 1999, http://www.imt.unine.ch/ESPLAB/www/projects/Microcam/, pp. 1-16.

Nguyen, Clark, "Communications Applications of Microelectromechanical Systems," Proceedings, Sensors Expo, May 19-21, 1998, San Jose, CA. pp. 447-455.

Tearney, G.J. et al., "Scanning single-mode fiber optic catheter-endoscope for optical coherence tomography," Optics Letters, Apr. 1, 1996, vol. 21, No. 7, pp. 543-545.

Zeis, Michael et al., "Color Business Report," ISSN 1055-3339. Jul. 2002, p. 5.

Jacobsen, Stephen C., U.S. Appl. No. 12/487,495, filed Jun. 18, 2009.

Jacobsen, Stephen C., U.S. Appl. No. 12/487,481, filed Jun. 18, 2009.

Jacobsen, Stephen C.; U.S. Appl. No. 12/792,562, filed Jun. 2, 2010.

Jacobsen, Stephen C.; U.S. Appl. No. 12/896,731, filed Oct. 1, 2010.

Jacobsen, Stephen C.; U.S. Appl. No. 12/896,732, filed Oct. 1, 2010.

Jacobsen, Stephen C.; U.S. Appl. No. 12/896,737, filed Oct. 1, 2010.

Jacobsen, Stephen C.; U.S. Appl. No. 12/896,743, filed Oct. 1, 2010.

Jacobsen, Stephen C.; U.S. Appl. No. 12/938,672, filed Nov. 3, 2010.

Jacobsen, Stephen C.; U.S. Appl. No. 12/946,442, filed Nov. 15, 2010.

U.S. Appl. No. 12/487,481, filed Jun. 18, 2009; Stephen C. Jacobsen; office action dated Oct. 12, 2012.

U.S. Appl. No. 12/512,188, filed Jul. 30, 2009; Stephen C. Jacobsen; office action dated Nov. 19, 2012.

Obreja et al.; "Poly (vinyl-alcohol) Films for Microphotonics"; 2004, IEEE, pp. 1-4.

U.S. Appl. No. 13/940,791, filed Jul. 12, 2013; Stephen C. Jacobsen; office action dated Jun. 27, 2014.

Subrahmanyam et al; Lens Aberrations; A Text Book of Optics; Jan. 1, 2004; Chapter 9, pp. 199-200; ; S. Chand & Co. Ltd.

* cited by examiner

METHOD AND DEVICE FOR WAVELENGTH SHIFTED IMAGING

CLAIM OF PRIORITY

This application claims priority to U.S. Provisional Patent Application No. 61/111,162 which was filed on Nov. 4, 2008 and which is incorporated herein by reference in its entirety.

FIELD OF THE INVENTION

The present invention relates to the field of miniaturized imaging devices. More specifically, the present invention relates to a device having a light source capable of propagating a predetermined wavelength of light onto a target, a lens system configured to receive light reflected from the target, and a non-linear optical media disposed behind the lens system.

RELATED CASES

The present invention is related to U.S. Provisional Patent Application No. 61/247,892, U.S. patent application Ser. Nos. 10/391,489; 10/391,490; 11/810,702; 10/391,513; 11/292,902; and 12/079,741 and U.S. Pat. No. 7,166,537 all of which are incorporated herein by reference in their entireties.

BACKGROUND

Minimally invasive diagnostic medical procedures are used to assess the interior surfaces of an organ by inserting a tube into the body. The instruments utilized may have a rigid or flexible tube and provide an image for visual inspection and photography, but also enable taking biopsies and retrieval of foreign objects. Analysis of image data collected during the inspection and imaging of the interior of the body cavity is a critical component of proper diagnosis of disease and other related conditions.

Examples of imaging devices presently used to view portions of the body convert an optical image to an electric signal. Well known types of silicon-based imaging devices capable of converting an optical image into an electrical signal include, for example, a set of charge-coupled devices (CCD) or complementary metal-oxide-semiconductor (CMOS) sensors. Two important characteristics of silicon-based imaging devices, such as the CMOS devices, are high noise immunity and low static power consumption. Significant power is only drawn when the transistors in the device are switching between on and off states. Consequently, the devices do not produce as much waste heat as other forms of logic, for example transistor-transistor logic (TTL). Importantly, silicon-based solid state imaging devices, such as the CMOS device, can only effectively duplicating optical images resulting from incident or direct wavelengths of light ranging from approximately 400 nanometers to approximately 1000 nanometers.

Non silicon-based solid state imaging devices (e.g., solid stated imaging devices based on Indium Gallium Arsenide (InGaAs), Indium antimonide (InSb), Mercury Cadmium Telluride (HgCdTe) are capable of detecting wavelengths of light greater than 1000 nanometers. However, these types of imaging devices require external readout devices as additional circuit components that cannot be fabricated on the same substrate as the detectors. Some also require a cooling component for proper operation. For example, InSb devices can only effectively operate under cryogenic conditions (about 80 degrees K.). Additionally, the pixel size of the Indium Gallium Arsenide (InGaAs) device is an order of magnitude greater than CMOS devices. Accordingly, certain optical components used in the imaging system must be larger to compensate, thereby increasing the cost, size, and weight of the overall optical system.

SUMMARY OF THE INVENTION

It has been recognized that it would be advantageous to develop an improved micro-camera catheter device capable of capturing images using non-visible wavelengths of light while still maintaining the benefits of using silicon-based image sensors.

According to one embodiment of the present invention, a micro-camera catheter device is disclosed comprising at least one light source disposed on a distal end of a catheter. The light source is capable of propagating a predetermined wavelength of light with a wavelength between approximately 1000 nanometers and approximately 2000 nanometers onto a target. The device further comprises a lens system disposed on the distal end of the catheter. The lens system is configured to receive light reflected from the target. The device further comprises a non-linear optical media disposed behind the lens system wherein the non-linear optical media is configured to modify the light reflected from the target. The device also comprises a silicon-based solid state imaging device (SSID) disposed behind the non-linear optical media. The silicon-based SSID is configured to receive light from the non-linear optical media. In one aspect of the invention, the silicon-based SSID is essentially free of Gallium Arsenide.

In one embodiment of the invention, the lens system comprises a GRIN lens and the non-linear optical media comprises a non-linear optical crystal. In one aspect, the non-linear optical crystal consists of lithium niobate, potassium titanyl phosphate, or lithium triborate. In one aspect, the non-linear optical media comprises a film formed on the silicon-based solid state imaging device. In yet another aspect, the non-linear optical media comprises a film disposed on a proximal end of the lens system. In yet another aspect, the non-linear optical media comprises a film disposed on the SSID sensor.

In one embodiment of the present invention, the micro-camera catheter device further comprises a plurality of light sources configured to simultaneously propagate a predetermined wavelength of light. In this aspect, the respective wavelengths of light from the different light sources are different. In an additional embodiment, the device further comprising a filter media configured to selectively pass predetermined wavelengths of light and reflect predetermined wavelengths of light.

In yet another embodiment of the present invention, a micro-camera catheter device is disclosed comprising a plurality of light sources disposed on a distal end of a catheter. The plurality of light sources are capable of simultaneously propagating a predetermined wavelength of light with a wavelength between approximately 1000 nanometers and approximately 2000 nanometers onto a target. The device further comprises a GRIN lens disposed on the distal end of the catheter, said lens system configured to receive light reflected from the target. The device further comprises a non-linear optical crystal optically coupled to the lens system and a filter media optically coupled to the non-linear optical crystal. The filter media is configured to selectively pass predetermined wavelengths of light and reflect predetermined wavelengths of light. The device further comprises a silicon-based SSID optically coupled to the filter media.

In one aspect, each of the plurality of light sources are configured to propagate different wavelengths of light. In yet another aspect of the invention, the device comprises a plurality of GRIN lenses optically coupled to a plurality of silicon-based SSIDs.

According to an additional embodiment of the present invention, a method of imaging tissues using non-linear optical media is disclosed. The method comprises the step of propagating a predetermined wavelength of light onto a target tissue, said predetermined wavelength of light being greater than 1000 nanometers. The method further comprises receiving the predetermined wavelength of light reflected from the target tissue into and through a lens system and receiving the predetermined wavelength of light from the lens system into and through a non-linear optical media. The method further comprises modifying the predetermined wavelength of light and receiving at least a portion of the modified wavelength of light onto a silicon-based SSID.

In one aspect of the invention, the method further comprises simultaneously propagating a wavelength of light from a plurality of light sources, wherein the wavelength of light from each of the plurality of light sources is different. In yet another aspect, the method further comprises the step of selectively passing certain portions of the modified wavelength of light through a filter media and selectively reflecting certain portions of the modified wavelength of light off of a filter media.

In an additional aspect of the invention, the method further comprises the step of propagating a wavelength of light through a target media and onto the target tissue. In one aspect, the target media is blood. In yet another aspect of the invention, the method further comprises the step of propagating a wavelength of light through a first target tissue and onto a second target tissue.

In an additional embodiment, the method further comprises the step of simultaneously propagating an additional wavelength of light onto the target tissue, wherein said wavelength of light is less than approximately 1000 nanometers.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein.

DETAILED DESCRIPTION OF EXAMPLE EMBODIMENT(S)

Figure 1:
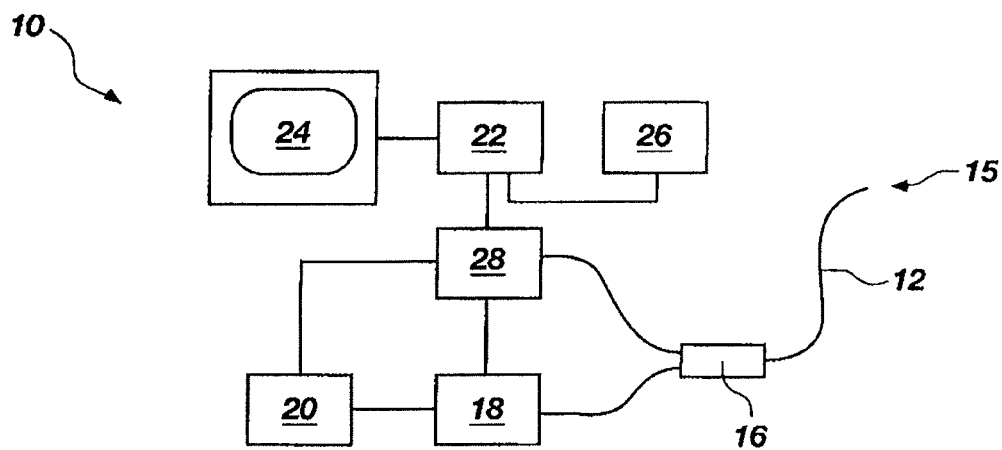
FIG. 1 is an exemplary view of a medical imaging system in accordance with an embodiment of the present invention.

Reference will now be made to, among other things, the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

It must be noted that, as used in this specification and the appended claims, singular forms of "a," "an," and "the" include plural referents unless the context clearly dictates otherwise.

An "SSID," "solid state imaging device," "SSID chip," or "solid state imaging chip" in the exemplary embodiments generally comprises an imaging array or pixel array for gathering image data. In one embodiment, the SSID can comprise a silicon or silicon-like substrate or amorphous silicon thin film transistors (TFT) having features typically manufactured therein. Features can include the imaging array, conductive pads, metal traces, circuitry, etc. Other integrated circuit components can also be present for desired applications. However, it is not required that all of these components be present, as long as there is a means of gathering visual or photon data, and a means of sending that data to provide a visual image or image reconstruction.

The term "silicon-based solid stated imaging device" or "silicon-based SSID" includes an SSID as described above which is substantially made from silicon or a silicon derivative. The silicon-based SSIDs do not produce as much waste heat as other SSIDs (such as InSb) and are configured to effectively duplicate optical images resulting from incident or direct wavelengths of light ranging from approximately 400 nanometers to approximately 1000 nanometers. In one aspect of the present invention, the silicon-based SSID is substantially free from any InGaAs materials.

The term "umbilical" can include the collection of utilities that operate the SSID or the micro-camera as a whole. Typically, an umbilical includes a conductive line, such as electrical wire(s) or other conductors, for providing power, ground, clock signal, and output signal with respect to the SSID, though not all of these are strictly required. For example, ground can be provided by another means than through an electrical wire, e.g., to a camera housing such as micromachined tubing, etc. The umbilical can also include other utilities such as a light source, temperature sensors, force sensors, fluid irrigation or aspiration members, pressure sensors, fiber optics, microforceps, material retrieval tools, drug delivery devices, radiation emitting devices, laser diodes, electric cauterizers, and electric stimulators, for example. Other utilities will also be apparent to those skilled in the art and are thus comprehended by this disclosure.

"GRIN lens" or "graduated refractive index lens" refers to a specialized lens that has a refractive index that is varied radially from a center optical axis to the outer diameter of the lens. In one embodiment, such a lens can be configured in a cylindrical shape, with the optical axis extending from a first flat end to a second flat end. Thus, because of the differing refractive index in a radial direction from the optical axis, a lens of this shape can simulate the effects of a more traditionally shaped lens.

With these definitions in mind, reference will now be made to, among other things, the accompanying drawings, which illustrate, by way of example, embodiments of the invention.

Turning to the drawings, in which like reference numerals represent like or corresponding elements in the drawings, in one embodiment of the present invention, FIG. 1 illustrates a medical imaging system 10 comprising a micro-catheter 12 having an imaging device disposed at a distal tip 15 of the micro-catheter 12. A processor 22, such as an appropriately programmed computer, is provided to control the imaging system 10 and create an image of anatomy adjacent the distal tip portion 15, within a patient (not shown), displayable on a monitor 24, and storable in a data storage device 26. An interface 28 is provided which supplies power to the imaging device 14 and feeds a digital image signal to the processor based on a signal received from the imaging device via an electrical umbilical, including conductive wires through the micro-catheter 12. A light source (discussed in more detail further below) may also be provided at the distal end of the micro-catheter 12. In one aspect, the system further includes a fitting 16 enabling an imaging fluid, such as a clear saline solution, to be dispensed to the distal tip portion of the micro-catheter 12 from a reservoir 18 through an elongated tubular member removably attached to the micro-catheter 12 or through a lumen of the micro-catheter 12 to displace body fluids as needed to provide a clearer image. Fluids may be pumped to the distal end of the micro-catheter for other reasons described herein. A pump 20 is provided, and is manually actuated by a medical practitioner performing a medical imaging procedure, or can be automated and electronically controlled so as to dispense fluid on demand according to control signals from the practitioner, sensors, or according to software commands.

Figure 2:
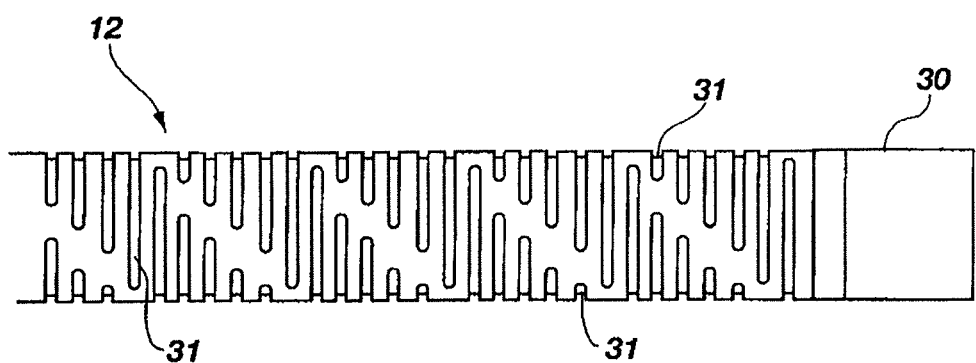
FIG. 2 is a side view of a micro-catheter in accordance with one embodiment of the present invention.
Figure 3:
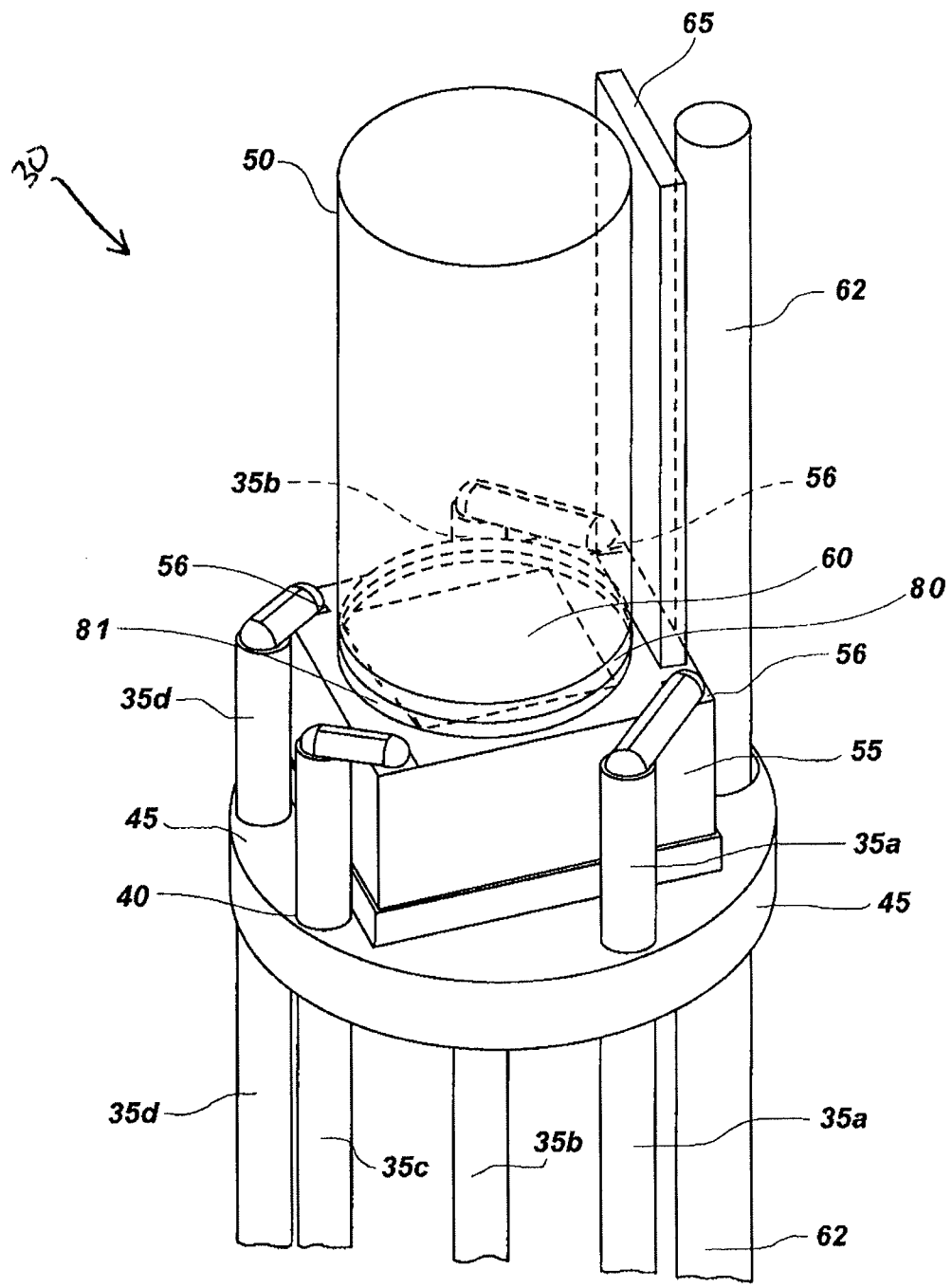
FIG. 3 is a perspective view of an imaging structure according to one embodiment of the present invention.

With reference now to FIGS. 2 and 3, according to one embodiment of the present invention, an imaging device 30 is disposed on a distal end of a micro-catheter 12. Micro-machined cuts 13 are disposed non parallel to a longitudinal direction of the micro-catheter 12 to enable a user, such as a medical practitioner, to guide and steer the distal end of the micro-catheter 12 within a cavity of a patient. In one aspect of the present invention, the micro-catheter may incorporate structure and principles of operation from a catheter disclosed in U.S. Pat. No. 6,014,919 to Jacobsen et al., which is incorporated herein by reference.

In one aspect of the invention, imaging device 30 comprises at least two conductive wires 35a, 35b for conducting electronic image data to the data processor 22 and for securing an imaging structure 30 between the at least two conductive wires 35a, 35b. As illustrated in FIG. 3 however, a plurality of conductive wires 35a, 35b, 35c, and 35d may be utilized. The at least two conductive wires 35a, 35b are oriented along a longitudinal axis of the imaging structure 30 and are disposed within alignment apertures 40 of a planar support member 45.

The planar support member 45 comprises at least two alignment apertures 40 disposed on opposing sides of the planar support member 45. The alignment apertures 40 are configured to receive and align the at least two conductive wires 35a, 35b along the longitudinal axis of the imaging structure 30. The imaging structure 30 is at least partially secured between the at least two conductive wires 35a, 35b and is disposed adjacent a top surface of the planar support member 45. In one aspect of the invention, the imaging structure 36 comprises a GRIN lens 50 optically coupled to a SSID 55 and disposed adjacent the SSID 55. The imaging structure further comprises an imaging array 60 disposed on a top surface of the SSID 55. In one embodiment, the GRIN lens 50 is positioned directly on top of the imaging array 60 of the SSID 55.

The at least two conductive wires 35a, 35b are operatively coupled to the imaging structure 30 and are configured to align the imaging structure 30 there between. In one aspect, the conductive wires 35a, 35b are bonded to the imaging structure 36 at contact points 56 disposed on the periphery of a top surface of the SSID 55. In yet another embodiment, the conductive wires 35a, 35b are bonded to a side surface of the SSID 55.

In one embodiment, the alignment apertures 40 are oriented perpendicular to the top surface of the planar support member 45. However, the alignment apertures may also be disposed in any orientation which is not non-parallel to the planar support member 45 as required to optimally align the imaging structure 30 as desired. In one embodiment, the imaging structure is mounted and aligned such that the image plane of the imaging structure 30 is non parallel to a longitudinal axis of the micro-catheter 12. In one aspect of the invention, a light source (e.g., a fiber optic member, LED, etc.) 62 is disposed within an aperture of the planar support member 45 to provide light for imaging. In yet another aspect of the present invention, the imaging structure 30 may incorporate structure and principles of operation from an imaging device disclosed in U.S. Pat. No. 7,166,537 to Jacobsen et al., which is incorporated herein by reference.

Figure 4:
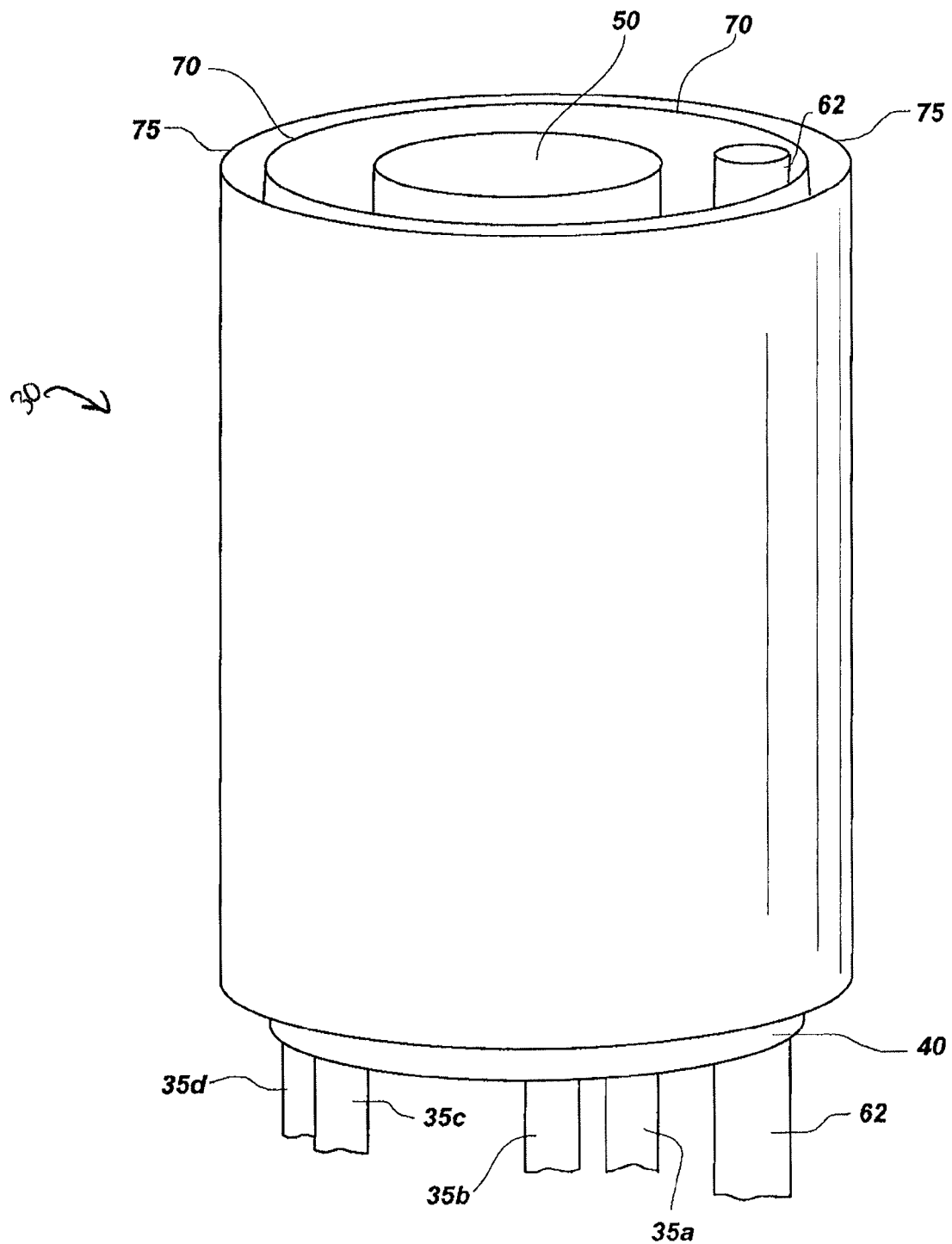
FIG. 4 is a perspective view of an imaging structure according to one embodiment of the present invention.

Referring now to FIGS. 3 and 4, the imaging device 30 further comprises a lens support member 65. In one aspect, the lens light shield 65 is bonded to a top surface of the SSID 55. In another aspect, the lens light shield 65 is bonded to a side surface of the SSID 55. In yet another aspect, the lens light shield 65 is bonded to a top surface of the planar support member 40. In any event, the lens support member 65 is oriented adjacent a side surface of the GRIN lens 50 to minimize stray light from entering the GRIN lens 50 during operation and to aid in proper alignment of the GRIN lens 50 on the imaging array 60 during operation and/or construction of the device. In one aspect of the invention, a first sleeve member 70 is disposed about the imaging structure 30. An adhesive is disposed within the first sleeve member 70 securing the components of the imaging structure 30 in place as well as securing the first sleeve member 70 to the imaging structure 30. In an additional embodiment, a second sleeve member 75 is disposed about the first sleeve member 70 and secured with an adhesive. In one aspect of the invention, the second sleeve member 75 comprises an opaque material to eliminate secondary light from impacting image quality.

In accordance with one embodiment of the present invention, the imaging device 30 incorporates and utilizes principles of nonlinear polarization as noted in more detail below.

In general, nonlinear polarization for a material can be expressed as $P = \chi^1 E^1 + \chi^2 E^2 + \chi^3 E^3 \ldots$ where P is the induced polarization, $\chi^n$ is the nth order no susceptibility, and E is the electric field vector. The first term describes the normal absorption and reflection of light; the second term describes the second harmonic generation (SHG) and sum and difference frequency generation; and the third, describes light scattering, stimulated Raman processes, third harmonic generation (THG), and both two- and three-photon absorption. SHG does not arise from an absorptive process. Instead, an intense laser field induces a nonlinear polarization in a molecule or assembly of molecules, resulting in the production of a coherent wave at exactly twice the incident frequency (half the wavelength). The magnitude of the SHG wave can be resonance enhanced when the energy of the photon energy of the second harmonic wave overlaps with an electronic absorption band. Principles of SHG, sum frequency generation (SFG), and difference frequency generation (DFG) may all be employed herein to optimize image quality resulting from use of infrared wavelengths of light reflected from a target and directed towards the silicon-based SSID 55.

An optical frequency multiplier is a nonlinear optical device, which creates the above referenced frequency output. Examples of non-linear optical media utilized to achieve frequency multiplication includes, but is not limited to, non-linear optical crystals or non-linear polymers. Examples of non-linear optical crystals contemplated for use with exemplary embodiments of the present invention include, but are not limited to, potassium titanyl phosphate ($KTiOPO_4$), Beta-Barium Borate ($\beta BaB_2O_4$), Potassium Dihydrogen Phosphate (KDP), Lithium triborate ($LiB_3O5$), and Potassium Dideuterium Phosphate (KD*P). Other possibilities include but are not limited to Lithium Niobate ($LINbO_3$), Magnesium Oxide Doped Lithium Niobate Crystals ($MgO:LiNbO_3$), Potassium Titanyl Phosphate (KTP), and KN ($KNbO_3$) which is a peoskite-type crystal.

In one aspect of the invention, the non-linear optical media comprises a film of silicon nanoparticle microcrystals such as those described in U.S. Pat. No. 6,585,947 to Nayfeh et al. which is incorporated herein by reference in its entirety. In one aspect of the invention, the film is deposited on a top surface of the silicon-based SSID 55. In yet another aspect, the film is deposited on a proximal (i.e., rear) end of the lens system 50. Advantageously, when the film (or other non-linear optical media discussed herein) is disposed on a proximal end of the lens system 50, material need not be deposited directly on the SSID. In this manner, there are no concerns regarding material interference with operation of the SSID 55 and its electrical components.

According to one embodiment of the present invention, an imaging device 30 is disclosed comprising at least one light source 62 disposed on a distal end 15 of a catheter 12 capable of propagating a predetermined wavelength of light onto a target. The wavelength of light propagated from the light source 62 ranges between approximately 1000 nanometers and approximately 2000 nanometers. The micro-camera catheter device further comprises a lens system 50 disposed on the distal end 15 of the catheter 12 as discussed in more detail above. The lens system 50 is configured to receive light reflected from the target. While specific reference to GRIN lenses are made herein, it is understood that any lens system may be used herein which has an optical output similar to that of a GRIN lens. In one aspect of the invention, a collimator (not shown) is disposed on a distal end of the lens system 50 to collect light reflected from the target and directed to the imaging system 10. The imaging device 30 further comprises a non-linear optical media 80 (such as the non linear crystals discussed above) disposed behind the lens system 50 and configured to modify the light reflected from the target and a silicon-based SSID 55 disposed behind the non-linear optical media 80. The silicon-based SSID 55 is configured to receive the modified light from the non-linear optical media 80. In on aspect, the non-linear optical media 80 may be disposed on the lens system 50 by an adhesive, such as an isobutyl/butyl acrylic copolymer, or other suitable means.

Advantageously, the non-linear optical media 80 acts as an optical frequency multiplier effectively shifting the wavelength of light propagated onto the target to a wavelength of light which the silicon-based SSID 55 is capable of detecting and converting into an electrical signal for imaging purposes. As noted above, current silicon-based SSID technology cannot effectively detect wavelengths of light greater than 1000 nanometers. Devices which are capable of detecting and imaging wavelengths of light greater than 1000 nanometers suffer from one or more disadvantages. However, one embodiment of the present invention allows for tissue and/or other target media, which may be more effectively imaged using wavelengths of light ranging from approximately 1000 nanometers to approximately 2000, to be imaged using well-developed silicon-based imaging technology. In sum, the end result of one embodiment of the present invention is a single wavelength of light which is capable of being detected by the silicon-based SSID 55 without the need for cooling devices or additional optical components to compensate for large pixel sizes. It is believed that longer wavelengths of light can feasibly be used with the camera disclosed herein, however the frequencies would have to be tripled rather than doubled. In one aspect of the invention, two non-linear optical devices may be placed in series to achieve a desired frequency multiplication effect.

In one aspect of the present invention, the light source 62 disposed on the distal end of the catheter 12 comprises a laser configured to emit a high-power short wave infrared laser beam, including, but without limitation, an InGaAsP MQW, DFB (Multiple Quantum Well Distributed Feed Back) laser diode. However, any light source capable of propagating wavelengths of light greater than 1000 nanometers is contemplated for use herein.

In another embodiment of the present invention the light source 62 disposed on the distal end of the catheter comprises an optical fiber and a light source coupled to the afore-mentioned fiber at a location remote to the distal end of the catheter.

In another embodiment of the present invention, the imaging device 30 further comprises a plurality of light sources (not shown) configured to propagate a predetermined wavelength of light onto a target surface. In this aspect, the respective wavelengths of light from the different light sources are different. The different wavelengths of light can be combined in the non-linear optical media 80 in a SFG and/or DFG process to produce a single wavelength of light which is capable of being detected by the silicon-based SSID 55 without the need for cooling devices or additional optical components to compensate for large pixel sizes.

In yet another embodiment, the imaging device 30 further comprises a filter media 81 configured to selectively pass predetermined wavelengths of light and reflect predetermined wavelengths of light. The filter media 81 is disposed on a proximal (i.e., rear) portion of the non-linear optical media 80 or on the face of the silicon-based SSID 55. In some instances, a wavelength of light reflected from a target may by slightly modified as it is reflected from the target. Advantageously, the filter media 81 minimizes interference from undesired wavelengths of light which might otherwise be detected by the silicon-based SSID 55.

According to one embodiment of the present invention, the filter media 81 comprises a dichroic media, such as a dichroic filter or a dichroic mirror. A dichroic filter is a color filter used to selectively pass light of a small range of wavelengths while reflecting others. By comparison, dichroic mirrors and dichroic reflectors tend to be characterized by the wavelengths of light that they reflect, rather than the wavelengths of light they pass.

In another embodiment of the present invention, the filter media 81 comprises an anti-reflective coating. The anti-reflective coating is applied to either a proximal (i.e., rear) and/or distal (i.e., front) of lens system 50. In another aspect, the anti-reflective coating is disposed on the face of the silicon-based SSID 55. In one aspect, the anti-reflective coating comprises a transparent thin film structure with alternating layers of contrasting refractive index. Layer thicknesses are chosen to produce destructive interference in the wavelengths of light reflected from the interfaces, and constructive interference in the corresponding transmitted wavelengths of light. This makes the structure's performance change with wavelength and incident angle, so that color effects often appear at oblique angles. In one aspect, a second quarter-wave thick higher-index layer is added between a low-index layer and a substrate. The reflection from all three interfaces produces destructive interference and antireflection. Additionally, varying thicknesses of the coatings may be used as desired.

In an additional aspect of the invention, an absorbing anti-reflection coating may be used. These coatings are useful in situations where high transmission through a surface is unimportant or undesirable, but low reflectivity is required. This type of coating can produce very low reflectance with few layers, and can often be produced more cheaply, or at greater scale, than standard non-absorbing anti-reflective coatings. Examples of materials used in absorbing anti-reflective coatings include titanium nitride and niobium nitride.

In yet another embodiment of the present invention, a phosphor coating may be applied directly to the SSID 55. In one aspect the phosphor coating comprises $Y_2O_2S:ErYb$, $YF_3:ErYb$, $NaYF_4:ErYb$, or other related wavelength conversion matrix as suits a particular application.

While reference has been made specifically herein to a single GRIN lens 50 used in connection with a single silicon-based SSID 55, it is understood and contemplated herein that a plurality of GRIN lens (not shown) could be used with a plurality of silicon-based SSIDs (not shown). In one aspect, each of the single GRIN lens/silicon-based SSID pairs is provided with a filter media 81 designed to pass and reflect different wavelengths of light and/or non-linear optical media 80. The filter media 81 associated with each of the GRIN lens/silicon-based SSID pairs could be designed to pass/reflect wavelengths of light which are different from a corresponding GRIN lens/silicon-based SSID pair. Advantageously, each GRIN lens/silicon-based SSID pair could receive light reflected from the same target but receive different wavelengths of light reflected from the target. In this manner, a composite image (or multiple images) could be created from the plurality of imaging devices receiving different wavelengths of light reflected from the same target. In one aspect, it is believed that a resulting composite image would have enhanced clarity. In another aspect, an optimal image may be selected from each of the GRIN lens/silicon-based SSID pairs and utilized for display of the target area. Similar modifications (i.e., multiple GRIN lens/silicon-based SSID pairs with different light polarization characteristics) could be made to the non-linear optical media 80 to suit a particular application. In one aspect of the invention, light source 62 is configured to selectively propagate different wavelengths of light at different intervals to accommodate the above contemplated invention.

Referring now generally to FIGS. 1 through 5, according to an additional embodiment of the present invention, a method of imaging tissues using a non-linear optical system is disclosed. The method comprises propagating a predetermined wavelength of light onto a target tissue wherein said predetermined wavelength of light being greater than 700 nanometers. The method further comprises receiving the predetermined wavelength of light reflected from the target tissue into and through a lens system 50. In one aspect of the invention, the lens system 50 is a GRIN lens. The method further comprises receiving the predetermined wavelength of light from the lens system 50 into and through a non-linear optical media 80. As noted above, the non-linear optical media may comprise a non-linear crystal such as potassium titanyl phosphate ($KTiOPO_4$), Beta-Barium Borate ($\beta BaB_2O_4$), Potassium Dihydrogen Phosphate (KDP), Lithium triborate ($LiB_3O5$), and Potassium Dideuterium Phosphate (KD*P). The method further comprises modifying the predetermined wavelength of light and receiving at least a portion of the modified wavelength of light onto a silicon-based SSID 55.

In yet another embodiment, the method further comprises simultaneously propagating a wavelength of light from a plurality of light sources (not shown), wherein the wavelength of light from each of the plurality of light sources is different. Alternatively, different wavelengths of light are propagated from a single light source at different time intervals.

In an additional aspect, the method further comprises the step of selectively passing certain portions of the modified wavelength of light through a filter media 81 and/or selectively reflecting certain portions of the modified wavelength of light off of a filter media 81. Advantageously, by propagating separate and distinct wavelengths of light onto an object, an optimal image may be obtained by selectively determining which wavelength of light results in an optimal image. Examplary techniques for determining image optimization include passive auto-focus techniques such as phase detection and/or contrast measurement.

In one embodiment of the invention, the method further comprises the step of propagating a wavelength of light through a target media, such as blood, and onto the target tissue. Because blood becomes transparent to wavelengths of light near 1550 nanometers, the light propagated at this wavelength would effectively "see through" the blood and reflect off of a target behind the blood. In like manner, other tissues exist which certain wavelengths of light may pass through. As such, the method further comprises the step of propagating a wavelength of light through a first target tissue and onto a second target tissue.

In an additional aspect of the invention, the method further comprises the step of simultaneously propagating an additional wavelength of light onto the target tissue, wherein said wavelength of light is less than approximately 700 nanometers (i.e., in the visible light spectrum). In this manner, an additional GRIN lens/silicon-based SSID may verify proper positioning and/or placement of the catheter 12 within portions of a subject.

While the forgoing examples are illustrative of the principles of the present invention in one or more particular applications, it will be apparent to those of ordinary skill in the art that numerous modifications in form, usage, material selection and details of implementation can be made without the exercise of inventive faculty, and without departing from the principles and concepts of the invention. Accordingly, it is not intended that the invention be limited, except as by the claims set forth below.

The invention claimed is:
1. A micro-camera catheter device, comprising:
  at least one light source disposed on a distal end of a catheter, said light source capable of propagating a predetermined wavelength of light with a wavelength between approximately 1000 nanometers and approximately 2000 nanometers onto a target;
  a circular lens system disposed on the distal end of the catheter, said lens system configured to receive light reflected from the target;
  a circular non-linear optical media disposed directly behind and in contact with the lens system, the non-linear optical media configured to modify reduce the wavelength of the light reflected from the target to below approximately 700 nanometers; and
  a circular linear optical disposed directly behind and in contact with the circular non-linear optical media; and
  a silicon-based solid state imaging device disposed behind the linear optical media, said silicon-based solid state imaging device configured to receive light from the linear optical media, wherein the outer circumference of the circular lens, circular non-linear optical media and linear optical media are substantially the same, wherein the non-linear optical media comprises a non-linear optical crystal.

2. The micro-camera catheter device of claim 1, wherein the lens system comprises a GRIN lens.

3. The micro-camera catheter device of claim 1, wherein the non-linear optical crystal is selected from the group consisting of lithium niobate, potassium titanyl phosphate, and lithium triborate.

4. The micro-camera catheter device of claim 1, wherein the non-linear optical media comprises a non-linear optical polymer.

5. The micro-camera catheter device of claim 1, further comprising a plurality/of light sources configured to propagate a predetermined wavelength of light, wherein the respective wavelengths of light from the different light sources are different.

6. The micro-camera catheter device of claim 1, further comprising a filter media configured to selectively pass predetermined wavelengths of light and reflect predetermined wavelengths of light.

7. The micro-camera catheter device of claim 1, wherein the non-linear optical media comprises a film formed on the silicon-based solid state imaging device.

8. The micro-camera catheter device of claim 1, wherein the non-linear optical media comprises a film disposed on a proximal end of the lens.

9. A micro-camera catheter device, comprising:
   a plurality of light sources disposed on a distal end of a catheter, said light sources capable of propagating a predetermined wavelength of light with a wavelength between approximately 1000 nanometers and approximately 2000 nanometers onto a target;
   a GRIN lens disposed on the distal end of the catheter, said lens system configured to receive light reflected from the target;
   a non-linear optical crystal film deposited on a proximal end of the GRIN lens, the film having an outer circumference substantially the same as an outer circumference of the GRIN lens, said non-linear optical crystal film being configured to reduce the wavelength of the light reflected from the target to below approximately 700 nanometers;
   a filter media having an outer circumference substantially the same as the outer circumference of the non-linear optical crystal film disposed directly behind the non-linear optical crystal film, said filter media being configured to selectively pass predetermined wavelengths of light and reflect predetermined wavelengths of light; and
   a silicon-based solid state imaging device optically coupled to the filter media.

10. The micro-camera catheter device of claim 9, wherein each of the plurality of light sources are configured to propagate different wavelengths of light.

11. The micro-camera catheter device of claim 9, comprising a plurality of GRIN lenses optically coupled to a plurality of silicon-based solid state imaging devices.

12. A method of imaging tissues using non-linear optical media, comprising:
   propagating a first predetermined wavelength of light onto a target tissue, said predetermined wavelength of light being greater than 1000 nanometers;
   receiving the predetermined wavelength of light reflected from the target tissue into and through a first lens system;
   receiving the predetermined wavelength of light from the first lens system into and through a non-linear optical media disposed directly behind and in direct contact with the first lens system, the non-linear optical media being configured to reduce the wavelength of light that passed through the first lens system; wherein the non-linear optical media comprises a non-linear optical crystal;
   reducing the wavelength of the predetermined wavelength of light to below approximately 700 nanometers;
   receiving at least a portion of the modified wavelength of light onto a silicon-based solid state imaging device;
   simultaneous to the propagation of the first wavelength of light, propagating a second wavelength of light onto the target tissue, wherein said second wavelength of light is less than approximately 700 nanometers;
   receiving, said second wavelength of light through a second lens system;
   generating a first image from the first wavelength of light; and
   generating a second image from the second wavelength of light.

13. The method of claim 12, further comprising simultaneously propagating a plurality of wavelengths of light from a plurality of light sources, wherein the wavelengths of light from each of the plurality of light is different.

14. The method of claim 12, further comprising the step of selectively passing certain portions of the modified first wavelength of light through a filter media.

15. The method of claim 12, further comprising the step of selectively reflecting certain portions of the modified first wavelength of light off of a filter media.

16. The method of claim 12, further comprising the step of propagating the first wavelength of light through a target media and onto the target tissue and propagating the second wavelength of light onto the target media.

17. The method of claim 16, wherein the target media is blood.

18. The method of claim 12, further comprising the step of propagating a wavelength of light through a first target tissue and onto a second target tissue.

19. A micro-camera catheter device, comprising:
   at least one light source disposed on a distal end of a catheter, said light source capable of propagating a plurality of predetermined wavelengths of light between approximately less than 700 nanometers and approximately 2000 nanometers onto a target at different time intervals;
   a first lens system disposed on the distal end of the catheter, said first lens system configured to receive light reflected from the target;
   a non-linear optical media disposed directly behind and in direct contact with the first lens system, the non-linear optical media configured to increase the frequency of the light reflected from the target, wherein the non-linear optical media comprises a non-linear optical crystal;
   a silicon-based solid state imaging device disposed behind the non-linear optical media, said silicon-based solid state imaging device configured to receive light from the non-linear optical media;
   a second lens system disposed on the distal end of the catheter, said second lens system configured to receive light reflected from the target;
   a second silicon-based solid state imaging device disposed behind the second lens system; and
   a processor and a display configured to display the image resulting from the light reflected from the target onto the first and second silicon-based solid state imaging devices.

20. The method of claim 19, wherein the light source is located away from the distal end of the catheter and an optical fiber is used to propagate the light to the proximal end of the catheter.

21. A micro-camera catheter device, comprising:
a first layer including a solid state imaging device having an imaging array disposed on a top surface of the solid state imaging device;
a second layer disposed on top of the first layer comprising a filter media configured to selectively pass certain wavelengths of light and reflect other wavelengths of light, wherein the filter media comprises an anti-reflective coating with alternating layers of contrasting reflective index;
a third layer disposed on top of the second layer comprising a two non-linear optical devices placed in series configured to increase the frequency of light passing through a lens system;
a fourth layer disposed on top of the third layer comprising the lens system; and
a light source configured to propagate different wavelengths of light at different time intervals.

\* \* \* \* \*